(12) United States Patent
Kämäräinen et al.

(10) Patent No.: US 11,461,914 B2
(45) Date of Patent: Oct. 4, 2022

(54) MEASURING SURFACE DISTANCES ON HUMAN BODIES

(71) Applicant: Sizey Oy, Espoo (FI)

(72) Inventors: Joni Kämäräinen, Tampere (FI); Song Yan, Tampere (FI); Johan Wirta, Espoo (FI)

(73) Assignee: Sizey Oy, Espoo (FI)

( * ) Notice: Subject to any disclaimer, the term of this patent is extended or adjusted under 35 U.S.C. 154(b) by 0 days.

(21) Appl. No.: 16/972,165

(22) PCT Filed: Jun. 3, 2019

(86) PCT No.: PCT/FI2019/050422
§ 371 (c)(1),
(2) Date: Dec. 4, 2020

(87) PCT Pub. No.: WO2019/234293
PCT Pub. Date: Dec. 12, 2019

(65) Prior Publication Data
US 2021/0241480 A1      Aug. 5, 2021

(30) Foreign Application Priority Data

Jun. 6, 2018 (FI) .................................. 20185517

(51) Int. Cl.
*G06T 7/60* (2017.01)
*G06T 17/20* (2006.01)

(52) U.S. Cl.
CPC .............. *G06T 7/60* (2013.01); *G06T 17/20* (2013.01); *G06T 2207/10028* (2013.01); *G06T 2207/30196* (2013.01)

(58) Field of Classification Search
None
See application file for complete search history.

(56) References Cited

U.S. PATENT DOCUMENTS 9,646,408 B2   5/2017 Johnson et al.
2010/0111370 A1* 5/2010 Black ..................... G06T 7/75
382/111

(Continued)

FOREIGN PATENT DOCUMENTS

EP      2819098 A1    12/2014
GB      2389500 A     10/2003

OTHER PUBLICATIONS

Aggeliki Tsoli; Matthew Loper; Michael J. Black; "Model-based anthropometry: Predicting measurements from 3D human scans in multiple poses;" IEEE Winter Conference on Applications of Computer Vision; Year: 2014 (Year: 2014).*

(Continued)

*Primary Examiner* — Edward Martello
(74) *Attorney, Agent, or Firm* — The Webb Law Firm

(57) ABSTRACT

Automatic anthropometric measurements may be utilised for various applications, such as online shopping and virtual tailoring. It is an objective to provide an apparatus for measuring surface distances of a human body. An apparatus is configured to receive a point cloud representing a surface shape of a scanned human body. The apparatus can be configured to generate a registered mesh of the surface shape of the scanned human body by registering a template mesh onto the point cloud. The template mesh can include predefined measurement paths, and the registered mesh can also include the predefined measurement paths after the registration. The apparatus can generate raw measurement results using the predefined measurement paths. The apparatus can be configured to calculate, using regression optimisation, at least one measurement result corresponding to a surface distance on the scanned human body using the raw measurement results.

17 Claims, 11 Drawing Sheets

(56) References Cited

U.S. PATENT DOCUMENTS

| | | |
|---|---|---|
| 2015/0009214 A1 | 1/2015 | Lee et al. |
| 2015/0213646 A1 | 7/2015 | Ma et al. |
| 2015/0262405 A1 | 9/2015 | Black et al. |
| 2016/0078663 A1 | 3/2016 | Sareen et al. |
| 2016/0203361 A1 | 7/2016 | Black et al. |
| 2017/0270709 A1 | 9/2017 | Tran et al. |

OTHER PUBLICATIONS

Tristan Fletcher; "Support Vector Machines Explained;" University College London, Gower Street, London, WC1E 6BT; 18 pages; 2008 (Year: 2008).*

Aggeliki et al. "Model-based anthropometry: Predicting measurements from 3D human scans in multiple poses", IEEE Winter Conference on Applications of Computer Vision, IEEE, Mar. 24, 2014, pp. 83-90.

Huang et al. "Block pattern generation: From parameterizing human bodies to fit feature-aligned and flattenable 3D garments", Computers In Industry, vol. 63, No. 7, Apr. 3, 2012, pp. 680-691.

Probst et al. "Efficient Model-Free Anthropometry from Depth Data", 2017 International Conference on 3D Vision (3DV), IEEE, Oct. 10, 2017, pp. 286-495.

Wang "CyberTape: an interactive measurement tool on polyhedral surface", computers and Graphics, vol. 28, No. 5, Oct. 1, 2004, pp. 731-745.

Weiss et al. "Home 3D body scans from noisy image and range data", 2011 IEEE International Conference on Computer Vision (ICCV), IEEE, Nov. 6, 2011, pp. 1951-1958.

Li et al. "Human Body Dimensions Extraction from 3D Scan Data", 2010 International Conference on Intelligent Computation Technology and Automation (ICICTA), IEEE, May 11, 2010, pp. 4441-4444.

* cited by examiner

| Measure | C | MAE [mm] | Success | Limit in mm [27] |
|---|---|---|---|---|
| *Male* | | | | |
| Ankle Circ. | 6 | 8.29 | 29% | 4 |
| Bicep Circ. | 8 | 6.14 | 57% | 6 |
| Calf Circ. | 6 | 3.16 | 79% | 5 |
| Chest Circ. | 5 | 15.12 | 63% | 15 |
| Elbow Circ. | 8 | 2.85 | 77% | 4 |
| Hip Circ. | 4 | 9.24 | 73% | 12 |
| Knee Circ. | 6 | 5.35 | 44% | 4 |
| NaturalWaist Circ. | 4 | 13.45 | 55% | 12 |
| NeckBase Circ. | 3 | 8.85 | 68% | 11 |
| Neck Circ. | 4 | 3.20 | 92% | 6 |
| Thigh Circ. | 8 | 8.31 | 44% | 6 |
| TrouserWaist Circ. | 3 | 9.29 | - | - |
| Wrist Circ. | 6 | 4.63 | 63% | 5 |
| Shoulder_to_Shoulder | 4 | 12.69 | - | - |
| Shoulder_to_Wrist | 6 | 12.87 | - | - |
| Avg. | | 8.23 | | - |
| *Female* | | | | |
| Ankle Circ. | 6 | 13.76 | 27% | 4 |
| Bicep Circ. | 8 | 4.75 | 72% | 6 |
| Calf Circ. | 6 | 3.86 | 79% | 5 |
| Bust Circ. | 3 | 12.70 | 69% | 15 |
| Elbow Circ. | 6 | 3.43 | 68% | 4 |
| Hip Circ. | 4 | 9.00 | 70% | 12 |
| Knee Circ. | 6 | 6.45 | 40% | 4 |
| NaturalWaist Circ. | 5 | 12.23 | 58% | 12 |
| NeckBase Circ. | 3 | 10.34 | 62% | 11 |
| Neck Circ. | 5 | 5.44 | 80% | 6 |
| Thigh Circ. | 8 | 8.13 | 47% | 6 |
| TrouserWaist Circ. | 3 | 16.19 | - | - |
| Wrist Circ. | 8 | 4.69 | 65% | 5 |
| UnderBust Circ. | 2 | 14.15 | 70% | 16 |
| Shoulder_to_Shoulder | 4 | 13.47 | - | - |
| Shoulder_to_Wrist | 4 | 14.44 | - | - |
| Bust_to_Bust | 9 | 11.51 | 55% | 10 |
| NeckSide_to_Wrist | 4 | 16.73 | - | - |
| NeckSide_to_Bust | 6 | 13.29 | 35% | 8 |
| Avg. | | 10.24 | | |

FIG. 11

| Measure | | | | Error (MAE) [mm] | | | | |
|---|---|---|---|---|---|---|---|---|
| | non-lin SVR | Ridge Regr | Lin Regr | Stepwise Regr | GPR | ElasticNet | BRDT | Multi-Tree | Lin SVR |
| *Male* | | | | | | | | | |
| Avg | 8.23 62% | 8.28 62% | 8.32 62% | 8.35 62% | 8.33 62% | 9.16 56% | 10.94 52% | 11.11 50% | 31.80 19% |
| *Female* | | | | | | | | | |
| Avg | 10.24 60% | 10.55 57% | 10.62 56% | 10.54 58% | 10.60 59% | 12.05 50% | 14.05 46% | 14.86 42% | 28.72 23% |

FIG. 14

MEASURING SURFACE DISTANCES ON HUMAN BODIES

CROSS-REFERENCE TO RELATED APPLICATIONS

This application is the United States national phase of International Application No. PCT/FI2019/050422 filed Jun. 3, 2019, and claims priority to Finnish Patent Application No. 20185517 filed Jun. 6, 2018, the disclosures of which are hereby incorporated by reference in their entirety.

BACKGROUND OF THE INVENTION

Field of the Invention

The present disclosure relates to measuring surface dimensions on human bodies. In particular, the present disclosure relates to measurement extraction using computer-implemented procedure.

Description of Related Art

Anthropometry may refer to the measurement of a human individual. Automatic anthropometric measurements may be utilised for various applications, such as online shopping and virtual tailoring. For example, a user may scan their body using an apparatus, and the apparatus may calculate various measurements related to the body shape of the user. Using these measurements, the user may, for example, purchase properly sized clothing form online stores, a tailor may manufacture a properly sized garment for the user, or the apparatus may manufacture a garment for the user. However, accurate measurements may require an expensive scanning device. Furthermore, these scanning devices are not always readily available for the end user. Automatic anthropometric measurements could be made more convenient and simple, if the relevant body measurements could be automatically determined by a device that most users already possess, such as a mobile phone. This may require obtaining reliable measurement from low-quality scans.

Some examples of prior art methods are included in US patent application US 2016/203361 A1. The aforementioned application discloses a method comprising: generating, based on data representing bodies of a first individual and a second individual, a first and a second set of attributes defining a first and a second parametric body models, and computing a similarity measure between the first set of attributes and the second set of attributes. A variety of attributes such as the gender, standard tailoring measurements and appropriate clothing sizes may be extracted from the fitted model.

SUMMARY OF THE INVENTION

It is an objective to provide an apparatus for measuring surface distances of a human body. The object is achieved by the features of the independent claims. Further implementation forms are provided in the dependent claims, the description and the figures.

According to the first aspect, an apparatus for measuring surface distances on human bodies comprises at least one processor and at least one memory comprising computer program code, wherein the at least one memory and the computer program code being configured to, with the at least one processor, cause the apparatus to at least: receive a point cloud representing a surface shape of a scanned human body; generate a registered mesh of the surface shape of the scanned human body by registering a template mesh, representing a reference shape of a human body, onto the point cloud, wherein the template mesh comprises predefined measurement paths, and wherein the registered mesh also comprises the predefined measurement paths; generate raw measurement results using the predefined measurement paths, wherein each raw measurement result in the raw measurement results corresponds to a measurement path in the predefined measurement paths; calculate, using regression optimisation, at least one measurement result corresponding to a surface distance on the scanned human body using the raw measurement results. With these configurations, the apparatus can, for example, accurately measure surface distances on a human body. Furthermore, the apparatus may be able to produce these measurements automatically, since the measurement paths are predetermined in the template mesh.

In an implementation form of the first aspect the apparatus further comprises at least one scanning device for scanning shapes of human bodies; wherein the at least one memory and the computer program code is further configured to, with the at least one processor, cause the apparatus to: use the scanning device for obtaining the point cloud. With these configurations, the apparatus can both scan a human body and measure surface distances on the human body based on the scan.

In a further implementation form of the first aspect, the regression optimisation com-prises one of: linear regression; stepwise linear regression; support vector regression, SVR; non-linear SVR; ridge regression; polynomial regression; stepwise regression; elastic net regression; Gaussian process regression; binary regression decision tree; and multi-regression tree. With these configurations, the apparatus may, for example, efficiently produce accurate estimates of surface distances on the scanned human body.

In a further implementation form of the first aspect, each measurement path in the predefined measurement paths comprises edges between vertices of the registered mesh. With these configurations, the apparatus may efficiently utilise the registered mesh and the edges of the registered mesh for the surface measurements.

In a further implementation form of the first aspect, the at least one memory and the computer program code is further configured to, with the at least one processor, cause the apparatus to, before generating the registered mesh: pre-align the point cloud and the template mesh. With these configurations, the apparatus may be able to better register the template mesh onto the point cloud, since misalignment between the point cloud and the template mesh may be reduced.

In a further implementation form of the first aspect, the at least one memory and the computer program code is further configured to, with the at least one processor, cause the apparatus to: pre-align a z-coordinate of a lowest point of the point cloud and a z-coordinate of a lowest point of the template mesh, wherein a z-axis is substantially parallel with a height direction of the scanned human body. With these configurations, the apparatus may be able to better pre-align the point cloud and the template mesh, since missing areas of the point cloud may affect the pre-alignment less.

In a further implementation form of the first aspect, each measurement path in the predefined measurement paths is indicated by a vertex identification, ID. With these configurations, the apparatus can, for example, efficiently identify vertices and edges that are part of a measurement path.

Furthermore, the same IDs may be used for both the template mesh and for the registered mesh.

In a further implementation form of the first aspect, the at least one memory and the computer program code is further configured to, with the at least one processor, cause the apparatus to: register the template mesh onto the point cloud using a non-rigid iterative closest point, ICP, procedure. With these configurations, the apparatus may be able to retain global convergence properties of ICP while introducing local non-rigid deformations, which may produce better registration.

In a further implementation form of the first aspect the at least one memory and the computer program code is further configured to, with the at least one processor, cause the apparatus to: register the template mesh onto the point cloud by determining a mapping that maps the template mesh onto the point cloud, wherein the mapping minimises a cost function. With these configurations, the apparatus can, for example, efficiently register the template mesh onto the point cloud.

In a further implementation form of the first aspect the cost function comprises a distance term, wherein the distance term comprises distances, wherein each distance in the distances corresponds to a distance between a point in the point cloud and a corresponding point in the template mesh. With these configurations, the apparatus can, for example, reduce the distance between corresponding point in the point cloud and in the template mesh, which may produce improved registration.

In a further implementation form of the first aspect the cost function further comprises a stiffness term, wherein the stiffness term indicates a similarity of transformations applied to neighbouring vertices of the template mesh in the mapping. With these configurations, the apparatus can, for example, reduce unwanted variations on the surface of the registered mesh. These variations may be caused, for example, by noise in the scanning process.

In a further implementation form of the first aspect, the apparatus is further configured to use the at least one measurement result in finding a fitting garment for the scanned human body. With these configurations, the apparatus or some other device can, for example, find a fitting garment for a user base on the scanned body of the user. Thus, the user can, for example, find well-fitting clothes without visiting a physical store. Instead, the user may use, for example, an e-commerce platform.

In a further implementation form of the first aspect, the apparatus is further configured to use the at least one measurement result in producing a garment for the scanned human body. This may allow, for example, producing garments having size and shape corresponding to the scanned human body. This may involve the apparatus itself comprising a sewing device for automatically producing the garment or the apparatus transmitting the measure to another apparatus, which may produce or facilitate producing the garment, for example by an automated sewing device.

According to the second aspect, a method comprises receiving a point cloud representing a surface shape of a scanned human body; generating a registered mesh of the surface shape of the scanned human body by registering a template mesh, representing a reference shape of a human body, onto the point cloud, wherein the tem-plate mesh comprises predefined measurement paths, and wherein the registered mesh also comprises the predefined measurement paths; generating raw measurement results using the predefined measurement paths, wherein each raw measurement result in the raw measurement results corresponds to a measurement path in the predefined measurement paths; calculating, using regression optimisation, at least one measurement result corresponding to a surface distance on the scanned human body using the raw measurement results.

According to the third aspect, a computer program is provided, comprising program code configured to perform a method according to the second aspect when the computer program is executed on a computer.

It is to be understood that the aspects and embodiments described above may be used in any combination with each other. Several of the aspects and embodiments may be combined together to form a further embodiment.

BRIEF DESCRIPTION OF THE DRAWINGS

The accompanying drawings, which are included to provide a further understanding and constitute a part of this specification, illustrate embodiments and together with the description help to explain the principles of the invention. In the drawings:

FIG. 11 illustrates a schematic representation of a table of measurement results according to an embodiment;

FIG. 14 illustrates a schematic representation of a table of measurement errors for various regressors according to an embodiment.

Like references are used to designate equivalent or at least functionally equivalent parts in the accompanying drawings.

DESCRIPTION OF THE INVENTION

The detailed description provided below in connection with the appended drawings is intended as a description of the embodiments and is not intended to represent the only forms in which the embodiment may be constructed or utilized. However, the same or equivalent functions and structures may be accomplished by different embodiments.

Figure 1:
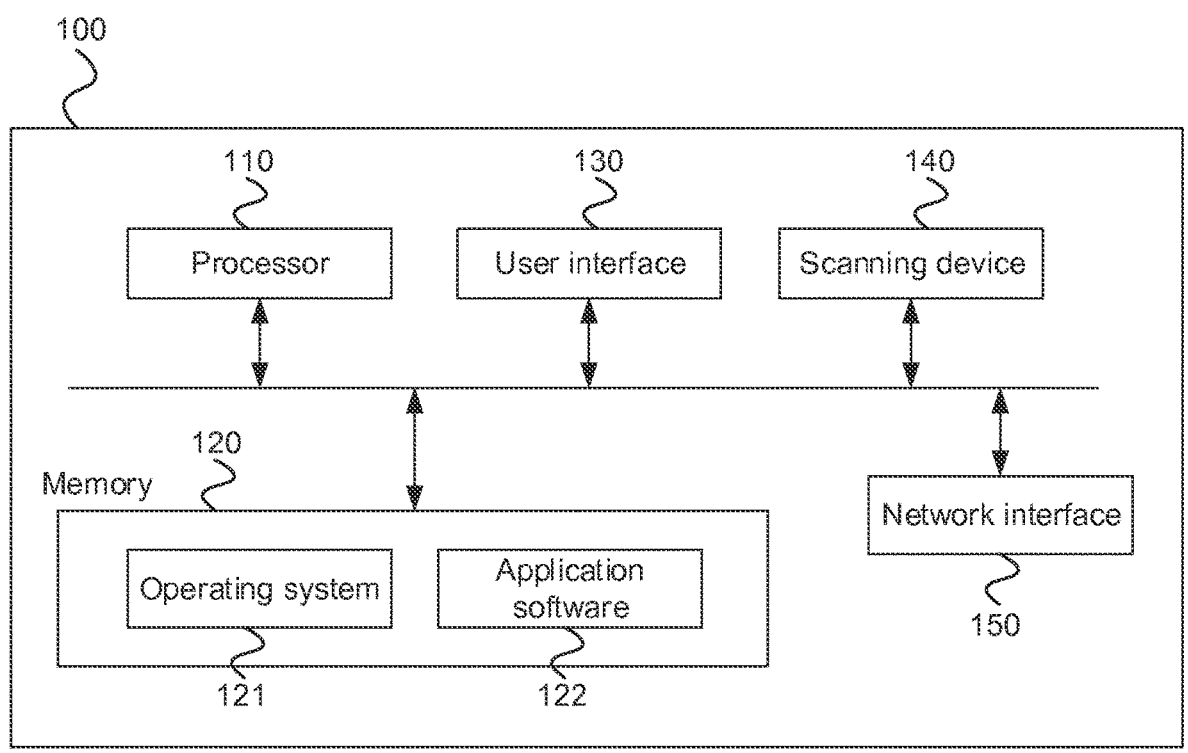
FIG. 1 illustrates a schematic diagram of an apparatus for measuring surface distances on a human body according to an embodiment.

FIG. 1 illustrates a schematic representation of an apparatus 100 for measuring surface distances on human bodies according to an embodiment. The apparatus 100 comprises at least one processor 110 and at least one memory 120 which comprises computer program code. The computer program code may include an operating system 121 and/or application software 122. The application software 122 may be used so that, when run on the operating system 121, it causes the at least one processor 110 to perform any or all of the operations described in the embodiments. The processor 110 can also be configured to coordinate any or all of the components 120, 121, 122, 130, 140, 150 of the apparatus 100 in order to perform scans using the one or more scanning devices 140, receiving input from a user via the user interface 130, if needed. In other embodiments, user input can be replaced with automatically generated reference values or reference values obtained from an external source, for example through the network interface 150. The memory 120 may comprise template meshes or they may be provided to the apparatus 100 from an external source, for example through a network connection. The apparatus may comprise a network interface for providing network connections. The apparatus may further comprise a user interface 130 for inputting information such as additional information. For example, the user interface 130 may be a keyboard, a touch screen, a tracking device or any combination of these. The user interface 130 may be configured to receive input from a user, which may provide one or more measurements corresponding surface distances, including circumferences, on the scanned human body.

According to an embodiment, the at least one memory 120 and the computer program code can be configured to, with the at least one processor 110, cause the apparatus 100 to at least receive a point cloud representing a surface shape of a scanned human body. The apparatus 100 may further generate a registered mesh of the surface shape of the scanned human body by registering a template mesh, representing a reference shape of a human body, onto the point cloud. The template mesh comprises predefined measurement paths, and the registered mesh also comprises the predefined measurement paths, since the registered mesh is generated from the template mesh. The apparatus may further generate raw measurement results using the predefined measurement paths. Each raw measurement result in the raw measurement results corresponds to a measurement path in the predefined measurement paths. The apparatus may further calculate, using regression optimisation, at least one measurement result corresponding to a surface distance on the scanned human body using the raw measurement results.

According to a further embodiment, the apparatus 100 comprises at least one scanning device 140 for scanning shapes of human bodies; wherein the at least one memory 120 and the computer program code is further configured to, with the at least one processor 110, cause the apparatus to: use the scanning device for obtaining the point cloud.

The at least one scanning devices 140 can be configured to provide information of the point cloud or information suitable for generating the point cloud. Such suitable information can be, for example, information suitable for generating three-dimensional images or images suitable for generating a three-dimensional mesh representation of a surface of a body. Any artefacts such as scanning platform or walls may be removed from the information before it is provided to the apparatus 100 or the processor 110, or the memory 120 may comprise instructions to remove the artefacts. The information may be provided from the scanning device 140 already in a form of the point cloud or it may be processed using the processor 110 to generate the point cloud. For example, the scanning device 140 may comprise a user interface and/or application software of its own. The information may also be provided by other means, for example, from an external source through the network interface 150. In an embodiment, the information is provided as images or body scans obtained by user devices such as mobile imaging devices and delivered to the apparatus 100, for example through the network interface 150.

Any three-dimensional, 3D, representation of a human body may be used to generate the point cloud. The information may correspond to any surface shape the scanned body including the whole body or a part of the body. The information may be directly in the form of a point cloud or it may be applicable for generating a point cloud. The information is therefore applicable for generating or providing a point cloud representing a surface shape of a scanned human body. The point cloud may comprise, for example 10000-100000 points in a three-dimensional coordinate system, such as the Cartesian system with x-, y- and z-coordinates. The point cloud can then represent the scanned body onto which a model of a human body, such as the template mesh, is to be fitted. Notably, the point cloud may comprise imperfections not directly corresponding to the actual human body such as features due to clothes, noise, or it may comprise shadow areas where the scanning device 140 has not been able to determine the features of the scanned human body precisely.

The scanning device 140 may, for example, be a scanning station. It may comprise a rotating base on top of which the target human body is positioned, for example in a standing position. The scanning device 140 may comprise one or more vertical pillars. One or more of the pillars may comprise one or more imaging devices such as scanners, which may be positioned at different heights. As an embodiment, three scanners may be used to provide an accurate three-dimensional scan. The scanners may output data in a mesh form, for example, as Wavefront OBJ files. The data may be rotated and/or scaled to match the reference point clouds or the candidate point clouds generated during the procedure. One or more pillars may also comprise one or more lighting devices. One or more of the pillars may also be used for providing support, for example for the person (the target human body) positioned on the rotating base. The scanning device 140 may be configured to provide a scan of the body, including a full-body scan, after a rotation of 360 degrees or more of the rotating base.

Since the apparatus 100 can generate the raw measurement results based on the predefined measurement paths and calculate the measurement result based on the raw measurement results, the process of measuring surface distances on a scanned human body can be automated. The apparatus 100 may utilise multiple raw measurement results via regression optimisation. For example, there may be a plurality of predefined measurement paths for a single measurement, and the apparatus 100 may utilise raw measurement results from all of the measurement paths in order to produce an accurate measurement result.

Any point clouds according to embodiments may correspond to a mesh, which may be a surface mesh. Even as a surface mesh, the mesh represents a human body or a part of a human body and is therefore three-dimensional. The points of the point cloud may then correspond to the vertices of the mesh. A mesh may be a triangular mesh so that the triangles, formed between the vertices form a surface corresponding to an approximation of a surface of a human body.

According to an embodiment, the apparatus 100 may be, for example, a mobile phone. In such embodiment, the scanning device 140 may be, for example, a camera of the mobile phone. Modern mobile phones may even comprise multiple cameras which may all be utilised. This may produce, for example, additional depth information for the scan. Alternatively or in addition to this, other sensors of the mobile phone may be used for the scanning, and inputs from different sensors may be combined for the scanning. Other sensors may be, for example, infrared, IR, sensors. Alternatively, a mobile phone may function as the scanning device 140, and another device, such as a server, may implement the other functionality based on scanning information obtained from the mobile phone.

According to an embodiment, the at least one measurement result is used in finding a fitting garment for the scanned human body. This may allow a user to find a fitting garment, for example, using an e-commerce platform.

According to a further embodiment, the at least one measurement result is used in producing a garment for the scanned human body. For example, the apparatus 100 can further comprise or be connected to, optionally through the network interface 150, to a device for producing garments. The device may be a sewing device, for example an automated sewing device. Alternatively, the apparatus 100 may send the at least one measurement result, for example, to a tailor who can manufacture the garment. This allows both the process of providing the measures and producing a garment based on the measures to be automated.

Figure 2:
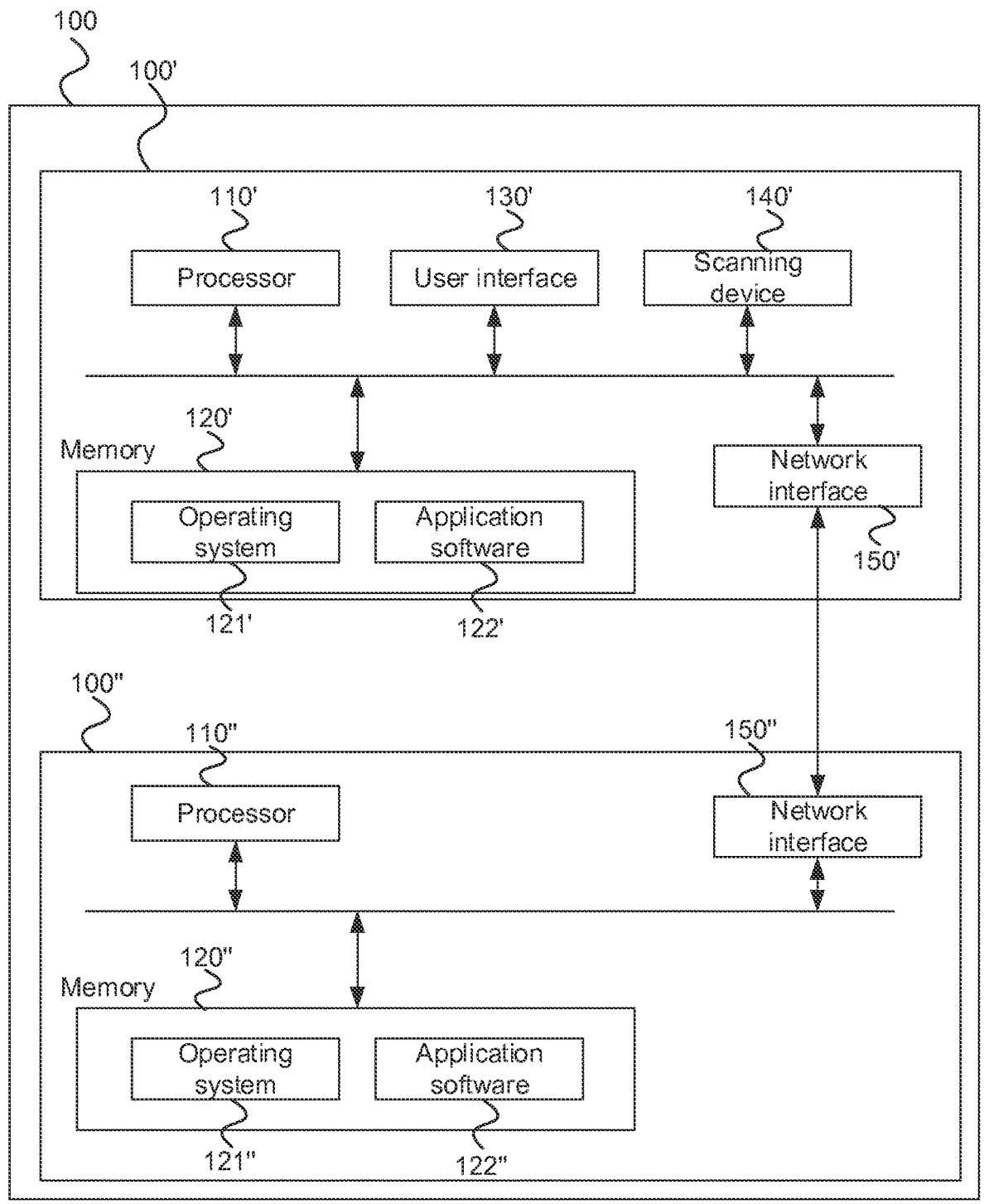
FIG. 2 illustrates a schematic diagram of an apparatus for measuring surface distances on a human body according to another embodiment.

FIG. 2 illustrates a schematic representation of an apparatus 100 comprising a local device 100' and a remote device 100" such as a server. In this way, part of the functions of according to the embodiments may be performed locally and part of the functions according to the embodiments may be performed remotely. For example, scanning of the target human body may be performed in the local device 100' and related information may be transmitted to the remote device 100" for processing. The local device 100' may be a, for example, a dedicated scanner, a mobile phone, or any other device. Also, data analysis may be performed in the remote device 100". Any additional information may also be stored in the remote device 100". Results of analysis, such as a three-dimensional mesh representation, may be transmitted from the remote device 100" to the local device 100', for example by using the network interfaces 150', 150". This way, the results may be visualized and/or measures may be determined in the local device 100'. It is also possible to determine at least part of the measurement results in the remote device 100". The measurement results determined this way may then be transmitted from the remote device 100" to the local device 100', for example by using the network interfaces 150', 150". Both the local device 100' and the remote device 100" may comprise any of the features described herein for the apparatus 100. The apparatus 100 may comprise one or more remote devices 100", for example servers or cloud computing apparatuses.

The apparatus 100 may comprise several devices and the functions of the apparatus may be split between the devices. For example, receiving input information may take place in one or more devices. Subsequently, the analysis of the input information, may be performed, for example, in the scanning device 140, in a local device receiving the input information or in a remote server where the input information is transmitted from a local device through a communications network. Correspondingly, producing the measurement result may be performed in a scanning device, in a local device receiving the input information or in a remote server where the input information is transmitted from a local device through a communications network.

Figure 3:
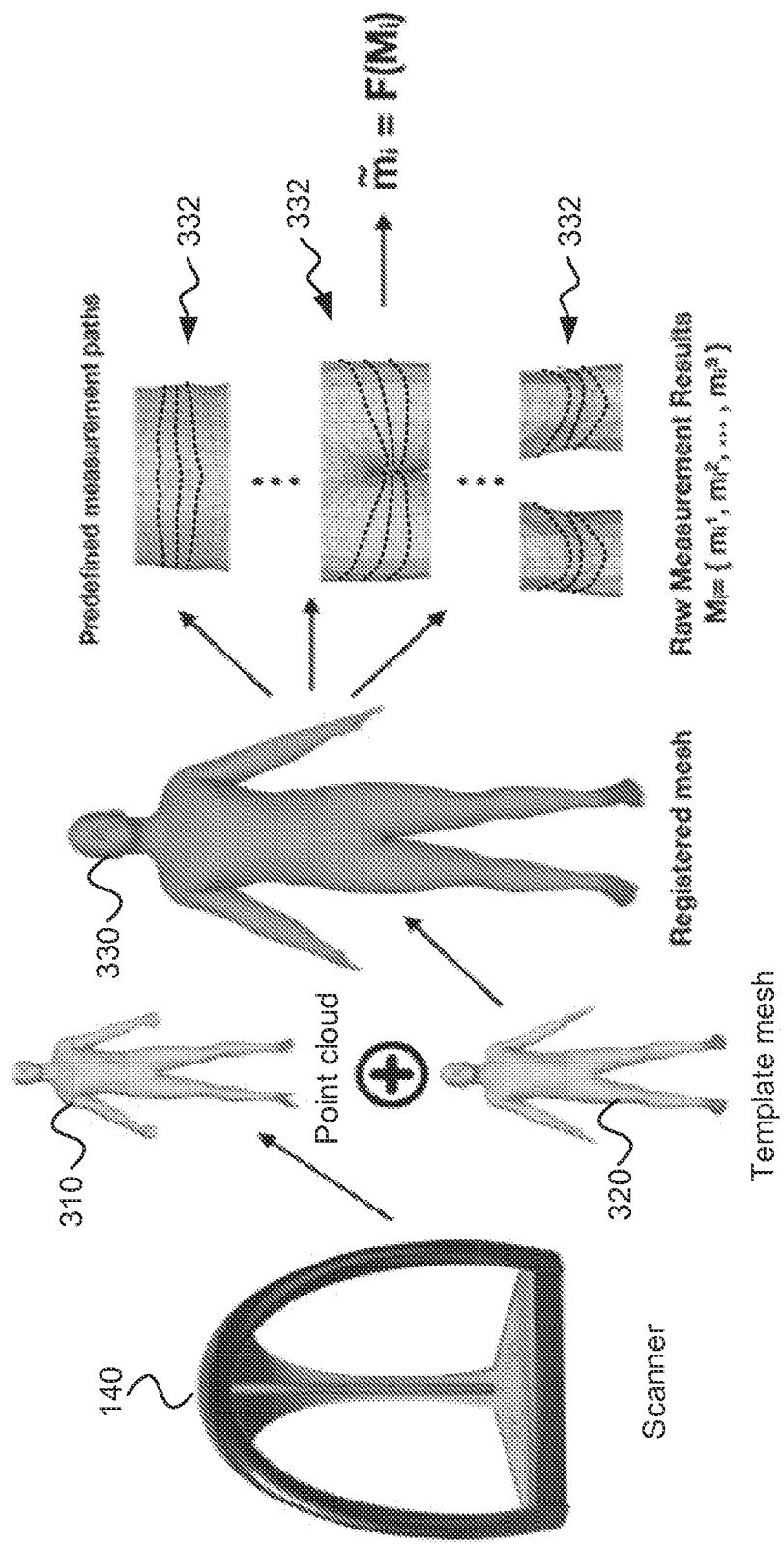
FIG. 3 illustrates a schematic diagram of a measurement procedure according to an embodiment.

FIG. 3 illustrates a schematic representation of a measurement procedure according to an embodiment. The procedures illustrated in FIG. 3 may be executed by the apparatus 100. Using a scanning device 140, a point cloud 310 is produced. The point cloud 310 represents the surface of a scanned human body. The point cloud 310 comprises a plurality of points, wherein each point may be assigned a coordinate in, for example, a Cartesian coordinate system. A template mesh 320, also referred to as an initial template, is registered onto the point cloud 310, which produces a registered mesh 330.

A mesh may comprise a plurality of vertices, wherein the location of the vertices and connections between the vertices, also referred to as edges, may define a geometrical shape, such as the surface area of a human body. A mesh may also comprise other components, such as a skeleton model and joints of such skeleton model.

In the registration, the template mesh 320 may be modified in such a fashion that the resulting registered mesh 330 substantially matches the point cloud 310. This may also be referred to as mapping: the template mesh 320 is mapped onto the point cloud 310. This registration/modification/mapping generates the registered mesh 330. Thus, the registered mesh 330 may represent the surface of the scanned human body. According to an embodiment, the apparatus 100 can register the template mesh onto the point cloud using a non-rigid iterative closest point, ICP, procedure.

The template mesh 320 comprises a plurality of predefined measurement paths 332. These measurement paths 332 may be indicated, for example, using the vertices of the template mesh 320. For example, a measurement path 332 may be indicated by a vector, wherein the vector comprises the identifications, IDs, of the vertices that the measurement path 332 comprises. After the registration process, also the registered mesh 330 comprises the plurality of measurement paths 332.

Based on the measurement paths 332 on the registered mesh 330, raw measurement results can be produced, wherein the raw measurement results may approximate physical measurements of the scanned human body. The raw measurement results may also comprise errors. The errors may have been produced during, for example, the scanning process or during the registration.

Regression optimisation can be used with the raw measurement results to produce measurement results corresponding to surface distances on the scanned human body. In the regression optimisation, multiple raw measurement results may be combined in order to produce a more accurate measurement result. For example, there may be three predefined measurement paths 332 around a single body part. This body parts may be, for example, an abdominal area, the waist, a thigh, or a knee of the scanned human body. Using the regression optimisation, N raw measurement results corresponding to N predefined measurement paths may be combined in order to produce a more accurate approximation of the desired measurement.

Since the template mesh 320, also referred to as a 3D human body model, is first fitted onto the point cloud 310 instead of making measurements directly from the point cloud 310 data, measurements can be done automatically. Measurements from the point cloud 310 data may also be sensitive to accurate alignment of the point cloud 310, point cloud noise or may even require manual verification of measurement paths. With a template mesh 320, the measurement paths can be fixed and predefined, for example, according to template mesh vertex IDs.

The template mesh 320 can be based on, for example, a 3D human body model, such as the MakeHuman model, the shape completion and animation of people, SCAPE, model, the BlendSCAPE model, or the skinned multi-person linear, SMPL model. These models may be based on data sets of scans of human bodies, such as the civilian American and European surface anthropometry resource project, CAE-SAR, data set. The CAESAR data set and additional scans have also been used to construct the SMPL model.

A problem with directly using data sets like CEASAR is that their optimisation can be non-linear and complex process and sensitive to initialisation. On the other hand, the models that have been created using these data sets, such as SCAPE, BlendSCAPE, and SMPL, can be linear in the shape space, and pose optimisation can be intuitive via skeleton joints.

The main principle of 3D human body shape models can be based on, for example, principal component analysis, PCA. A 3D shape model can be defined by a mean shape T and principal shape directions S. A specific body shape can be constructed as a linear sum of $|\beta|$ principal shape directions S added to the mean shape T:

$$T + B(\beta) = T + \sum_{n=1}^{|\beta|} \beta_n S_n.$$

As few as $|\beta|=10$ principal shape directions may provide sufficient accuracy for many applications. The next step may be to include a 3D pose to the model, which is typically achieved by assigning a skeleton to the shape model and each shape vertex location is related to a specific skeleton part. The shape deformation pose can be represented by assigning the 3D rotations θ of K skeleton joints. An important part of constructing an effective and efficient 3D human body model with shape deformation and pose parameters {T,S,θ} is the initial model, its registration to training data, and number and quality of training examples.

The SMPL mesh model contains N=6890 vertices (13766 faces) and K=23 skeleton joints. The mesh has the same topology for men and women, spatially varying resolution, a clean quad structure, a segmentation into parts, initial blend weights, and a skeletal rig. A particular detail that makes SMPL registration efficient is that it divides the shape deformation into a pose independent deformation $B_S(\beta)$ and a pose specific deformation $B_P(\theta)$ which are summed to define the final shape. Notably the shape deformation parameters can also be used to predict the rotations of the K=23 skeleton joints $J(\beta)$: $\mathbb{R}^{|\beta|} \mapsto \mathbb{R}^{3K}$.

Figure 4:
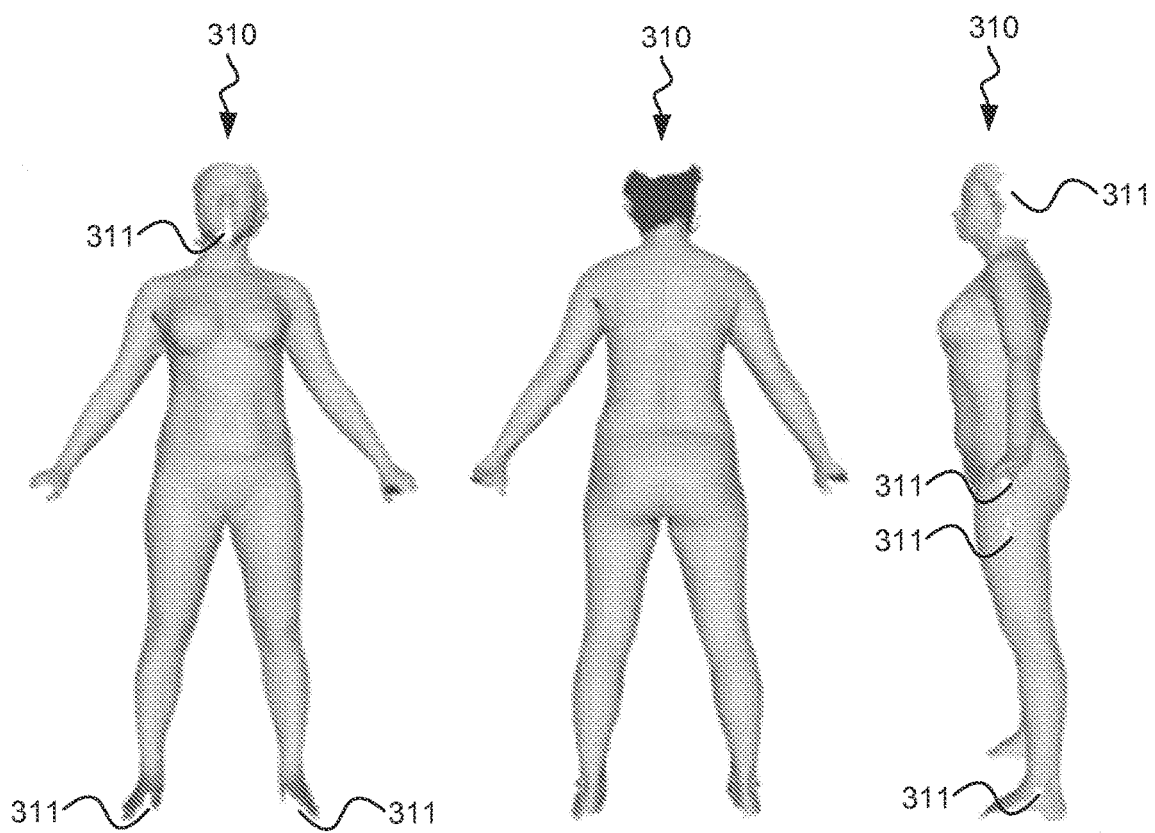
FIG. 4 illustrates a schematic representation of a point cloud representing a surface shape of a scanned human body according to an embodiment.

FIG. 4 illustrates a schematic representation of a point cloud 310 received from the scanning of a human body according to an embodiment. The point cloud 310 is illustrates from three directions in FIG. 4. As can be seen from the point cloud 310, some parts 311 of the scanned human body are missing from the point cloud 310. The missing parts 311 may also be referred to as holes. The missing parts 311 may be due to, for example, body part occlusion. For example, if the scanning is done optically, some body part may block the light source so that some body part is not light sufficiently for the scanning. Alternatively or in addition to this, some body part may block the line of sight of the scanning device 140 to some other body part. The missing areas 311 could cause issues, if the point cloud 310 was directly used for anthropometric measurements. For example, it could be difficult to assign a measurement result to a measurement path, if the measurement path was collocated with a missing part 311. Even if a measurement result is obtained in such a case, some error could be introduced, since there is no information available about the scanned human body in the missing parts 311.

There is also some visible noise in the point cloud 310 presented in FIG. 4 as can be seen from the roughness of the point cloud 310 in some areas. The noise may be produced by the scanning device 140. For example, if the scanning is done using a mobile phone, there may be more noise than if the scanning is done using a dedicated scanning device. The conditions during the scanning may also affect the amount of noise in a scan. For example, if the scanning is done in darker conditions, the point cloud 310 may comprise more noise than if the scanning is done is sufficient lighting. The noise could cause errors, if the point cloud 310 was directly used for anthropometric measurements. Since the point cloud 310 differs from the actual scanned human body due to the noise, measurements done on the point cloud 310 may not fairly represent measurements of the actual human body. For example, the surface roughness seen in the point cloud 310 of FIG. 4 may cause a measurement result to be larger than the actual measurement, since the measurement path can be longer on the point cloud due to the noise.

Figure 5:
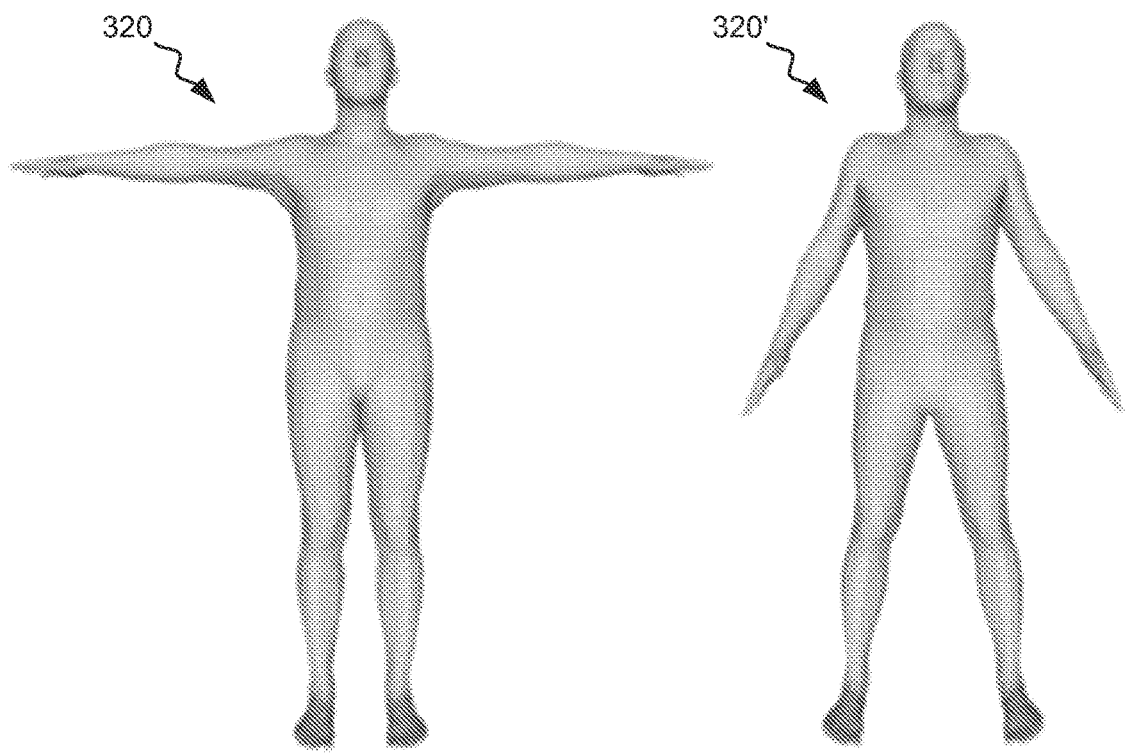
FIG. 5 illustrates a schematic representation of a template mesh according to an embodiment.

FIG. 5 illustrates a schematic representation of a template mesh according to an embodiment. When the template mesh 320 is registered onto the scanned point cloud 310, the stance of the template mesh 320 should be considered. A stance may also be referred to as a pose. For example, if the template mesh 320 illustrated in FIG. 5 is registered onto the point cloud 310 presented in FIG. 4, the resulting registered mesh 330 may not be satisfactory. Therefore, before the registration, the stance of the template mesh 320 may need to be adjusted to better match the scanned point cloud 310. A template mesh 320' with an adjusted mesh is also illustrated in FIG. 5. The template mesh 320 can also be adjusted to a predefined stance, and during the scanning process, the person to be scanned can be instructed to take a stance that substantially matches the initial zero-pose of the adjusted template mesh 320'. For example, the stance of the point cloud 310 presented in FIG. 4 can be considered to substantially match the stance of the adjusted template mesh 320' presented in FIG. 5.

Figure 6:
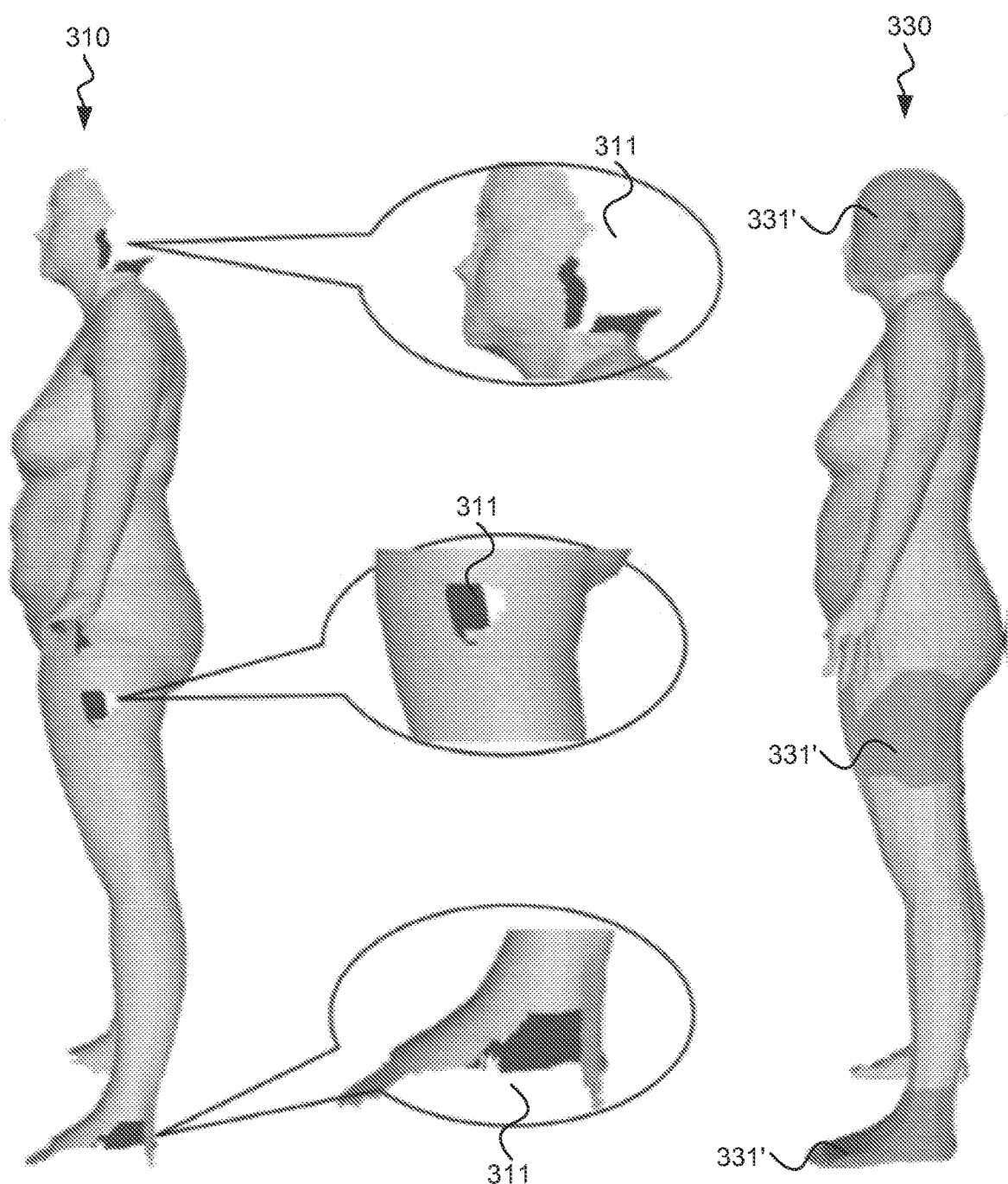
FIG. 6 illustrates a schematic representation of a point cloud and a corresponding registered mesh according to an embodiment.

FIG. 6 illustrates a schematic representation of a point cloud 310 comprising missing parts 311 and a corresponding registered mesh 330 according to an embodiment. As can be seen from FIG. 6, the registered mesh 330 does not comprise the missing parts 311, while the point cloud 310 comprises the missing parts 311. Herein, a "missing part" may refer to the empty areas in the point cloud 310. Instead, the corresponding areas 331' are substantially continuous in the registered mesh 330, and the registered mesh 330 comprises no visible holes. This can be considered to be due to the fact that as the template mesh 320 is registered onto the point cloud 310, the template mesh 320 fills the missing parts 311. It could be said that information comprised in the template mesh 320 about an average human body is used to fill the missing parts 310 during the registration process.

Since the registered mesh 330 may comprise no holes, conducting anthropometric surface measurements on the registered mesh 330 instead of the point cloud 310 may provide more reliable results. For example, if a missing part 331 would be collocated with a measurement path 332, it could be difficult to assign a measurement result to that path due to the missing part 311, if the measurement was done based on the point cloud 310. Since the registered mesh 330 does not comprise the holes 331, measurements done based on the registered mesh 330 may provide more reliable results even if a measurement path is collocated with a missing part 331. Furthermore, as can be seen from FIG. 6, the registered mesh 330 may comprise less noise than the point cloud 310. Thus, the registration process may reduce noise. This may result in more reliable measurement results, since the noise can also be reduced from the measurement paths 332 and the corresponding raw measurement results.

According to an embodiment, the shape of a point cloud $p_n=[p_{nx},p_{ny},p_{nz}]$ comprising n points may be stored as a vector $v=[p_{0x},p_{0y},p_{0z},p_{1x},p_{1y},p_{1z},p_{2z}, \ldots, p_{n-1z}]$, where each item corresponds to one coordinate (x,y,z) of one point. Alternatively, the point cloud may be stored, for example, in a matrix, where each row or column of the matrix may comprise the coordinates of a single point. It is appreciated by a person skilled in the art that the vectors may be expressed as row or column vectors and all the equations and other structures such as matrices can be formulated accordingly.

According to an embodiment, the at least one memory 120 and the computer program code is further configured to, with the at least one processor 110, cause the apparatus 100 to register the template mesh 320 onto the point cloud 310 using a non-rigid iterative closest point, ICP, procedure.

The ICP procedure does not set any strong assumptions on the inputs. ICP extensions and other novel approaches for surface registration may also be used. Non-rigid ICP approach may be appropriate due to the fact that this approach can explicitly handle holes 311 in the point cloud 310. The challenge is two-fold—it may be beneficial to retain the global convergence properties of ICP while introducing local non-rigid deformations. The global constraint can help the procedure to converge to a meaningful final output that can conserve the overall body shape of the scanned human body. On the other hand, local deformations may allow adaptation to specific details of each scanned human body.

According to an embodiment, the SMPL body model can be used as the template mesh 320. The starting point for the registering may be a pre-aligned model defined by $\{T,\beta_i, \theta_k\}_{i=1,\ldots,|\beta|,k=1,\ldots,K}$ that brings the SMPL template in approximate correspondence with the obtained scan point cloud $T_{scan}$. If the pre-aligned SMPL model is defined as V, then the problem may be to find values for the alignment parameters X so that V(X) projects the template mesh 320 onto the surface points $T_{scan}$.

According to an embodiment, the at least one memory 120 and the computer program code is further configured to, with the at least one processor 110, cause the apparatus 100 to register the template mesh 320 onto the point cloud 310 by determining a mapping that maps the template mesh 320 onto the point cloud 310, wherein the mapping minimises a cost function.

According to a further embodiment, the cost function comprises a distance term, wherein the distance term comprises distances, wherein each distance in the distances corresponds to a distance between a point in the point cloud 310 and a corresponding point in the template mesh 320.

According to a further embodiment, the cost function further comprises a stiffness term, wherein the stiffness term indicates a similarity of transformations applied to neighbouring vertices of the template mesh 320 in the mapping.

To solve the parameters X an energy function of three terms can be defined as follows:

$$E(X)=E_d(X)+\alpha E_s(X)+\beta E_l(X).$$

The energy function may also be referred to as a cost function. The energy function does not necessarily represent any physical energy, instead the energy function can be used as a tool in the registration process. $E_d$ may represent a distance term to measure the point-wise distances between the model V and the scan points $T_{scan}$.

$$E_d(X) = \sum_{v_i \in V} w_i dist^2(T_{scan}, X_i v_i),$$

where $X_i$ can be a linear mapping of a single model vertex $v_i$ of the SMPL model to correspondence in $T_{scan}$. $w_i$ defines whether a model point has a correspondence in the scan ($w_i=1$) or not ($w_i=0$). $E_s$ may be a local stiffness term:

$$E_s(X) = \sum_{i \in N_j} \|(X_i - X_j)\text{diag}(1,1,1,\gamma)\|_F^2,$$

where $\|\bullet\|_F^2$ is a matrix Frobenius norm, and $\text{diag}(1,1,1,\gamma)$ is a diagonal matrix with elements 1,1,1, and $\gamma$ on the diagonal of the matrix. The stiffness term can enforce similar transformations between neighbouring vertices $N_j$ of the model vertex $v_j$. $\gamma$ can be used to weight differences in the rotational and skew part of the deformation against the translational part of the deformation. For example, $\gamma=1$ in some embodiments. The third energy term is the landmark term $$E_l(X) = \sum_{v_i, l \in L} \|X_i v_i - l\|^2.$$

The landmarks L can be predefined and/or important positions in the model, the landmark term $E_l$ may enforce them to be registered particularly well.

Locally affine regularisation can assign an affine transformation to each vertex and minimize the difference in the transformation of neighbouring vertices. The deformation parameters X, which would be applied on source vertices to generate the target surface deformation, can be obtained by minimising the following cost function:

$$\overline{E}(X) = \left\| \begin{bmatrix} \alpha M \otimes G \\ WD \\ \beta D_L \end{bmatrix} X - \begin{bmatrix} 0 \\ WU \\ U_L \end{bmatrix} \right\|_F^2 = \|AX - B\|_F^2.$$

The cost function $\overline{E}(X)$ takes its minimum at $X=(A^TA)^{-1}A^TB$. In the above equation, M is the node-arc incidence matrix of the template mesh topology, $G:=\text{diag}(1,1,1,\gamma)$ is a weighting matrix. $W:=\text{diag}(w_1, \ldots, w_n)$ represents the weighting matrix in which $w_i=0$ if template vertices $v_i$ corresponds to missing data in the target mesh and n represents the number of template vertices. D is the sparse matrix of template vertices mapping the 4n×3 deformation parameters X. U is the matrix of the correspondence points on the target mesh, $D_L$ and $U_L$ are the predefined landmarks on the template mesh and their correspondence points on the target mesh respectively. The Kronecker product is denoted by $\otimes$. $\alpha$ is the stiffness term which can penalise differences between the transformation matrices assigned to neighbouring vertices, while the landmark weight β can be used to fade out the importance of the potentially noisy landmarks towards the end of the registration process. In some embodiments, the predefined landmarks may not be utilised. In such cases, $U_L$ and $D_L$ may not need to be considered.

The registration process may be implemented in the computer program code using, for example, two nested loops. In the outer loop a series of deformations of the template mesh 320 can be performed for each stiffness $\alpha^i \epsilon \{\alpha^1, \ldots, \alpha^n\}$, where $\alpha^i > \alpha^{i+1}$. These α values help the registration process to proceed from a global deformations to more localised ones. For example, $\alpha^1 = 100$, and the following values may be $\alpha^i = \alpha^{i-1} - 1$ so that the final value is $\alpha^{100} = 1$. In the inner loop, a deformation X for a fixed stiffness term i and preliminary correspondences can be found. Preliminary correspondences can be found by a nearest point search. The deformation X can be determined, for example, until $\|X^j - X^{j-1}\| < \epsilon$, where ε is a preconfigured threshold.

The registration process according to the invention can bring, for example, the following benefits: it can produce a hole-free registered meshes that can depreciate the influences caused by missing body parts and noise, and the registered meshes can be in the same topology structure as the template mesh, which facilitates to find the corresponding landmarks and predefined measurement paths for, for example, tailor measurements.

According to an embodiment, the at least one memory 120 and the computer program code is further configured to, with the at least one processor 110, cause the apparatus 100 to, before generating the registered mesh, pre-align the point cloud and the template mesh.

According to a further embodiment, the at least one memory 120 and the program code cause the apparatus 100 to pre-align a z-coordinate of a lowest point of the point cloud and a z-coordinate of a lowest point of the template mesh, wherein a z-axis is substantially parallel with a height direction of the scanned human body.

A pre-alignment procedure may be performed before the non-rigid ICP registration. Generally the misalignment of registration can be partly raised by wrong scales, face orientations, and the different centre points of subjects. To depreciate this, firstly all scans can be scaled into the same unit of measurement, such as metres, as template mesh 320. All scans can then be rotated to make sure that they face the same direction. All samples can be aligned into the same lowest point (Z-axis). Alternatively, the mean coordinate of vertices can be adopted as the centre points, and all meshes can be aligned into the same centre point. The centre points can change dramatically due to the missing parts on scans and can bring negative effects on registration. A standard point (x, y, 0) can be employed as the lowest point for all meshes. After the pre-alignment procedure, all scans and the SMPL models may be standing, for example, on the X-Y plane and facing to Y-axis direction with the same scale.

Figure 7:
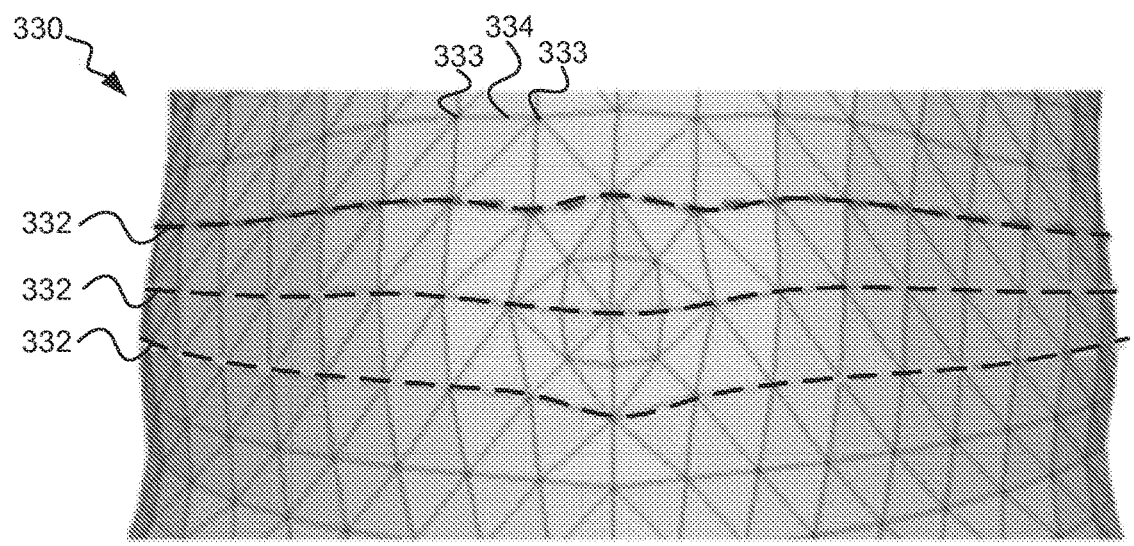
FIG. 7 illustrates a schematic representation of measurement paths around the abdomen of a registered mesh according to an embodiment.

FIG. 7 illustrates a schematic representation of measurement paths 332 around an abdomen of a registered mesh 330 according to an embodiment. Although "abdomen" and other similar terms can refer to a human body, these terms are used herein to refer to the corresponding areas in the point cloud 310, in the template mesh 320, and in the registered mesh 330. Three measurement paths 332 are presented in FIG. 7. All of the measurement paths 332 presented in FIG. 7 go around the abdomen area of the registered mesh 330. For each measurement path 332, a raw measurement result may be generated. In the regression optimisation procedure, the raw measurement results may be combined in order to generate, for example, a single measurement result which can be more accurate than the raw measurement results. The measurement paths 332 can be predetermined on the template mesh 320. However, the measurement paths 332 may move as the template mesh 320 is registered onto the point cloud 310, and this movement may be difficult to predict. Therefore, the use of a plurality of measurement paths 332 may ensure that when the raw measurement results are combined using the regression optimisation, the resulting measurement result is more accurate than the raw measurement results.

The term "measurement" may be used herein to refer to a quantity the value of which is to be obtained. A plurality of measurement paths 332 may be used for a single measurement. For example, in the case of the embodiment presented in FIG. 7, the measurement may be the abdominal circumference, and the measurement paths 332 may be used to obtain raw measurement results. The raw measurement results can be used, in turn, to obtain a measurement result which can approximate the value of the measurement.

As can be seen from FIG. 7, the registered mesh comprises vertices 333. Although the registered mesh 330 comprises a larger number of vertices 333, only two vertices 333 are indicated in FIG. 7 for clarity purposes. The two vertices 333 presented in FIG. 7 are connected by an edge 334. Although the registered mesh 330 comprises a larger number of edges 334, only one edge 334 is indicated in FIG. 7 for clarity purposes. Each raw measurement result may be calculated, for example, by summing the lengths of all edges that the corresponding measurement path comprises.

According to an embodiment, each measurement path in the predefined measurement paths 332 is indicated by a vertex identification, ID. For example, each measurement path 332 may be indicated by a vector of vertex IDs.

According to a further embodiment, each measurement path in the predefined measurement paths 332 comprises edges 334 between vertices 333 of the registered mesh 330.

Figure 8:
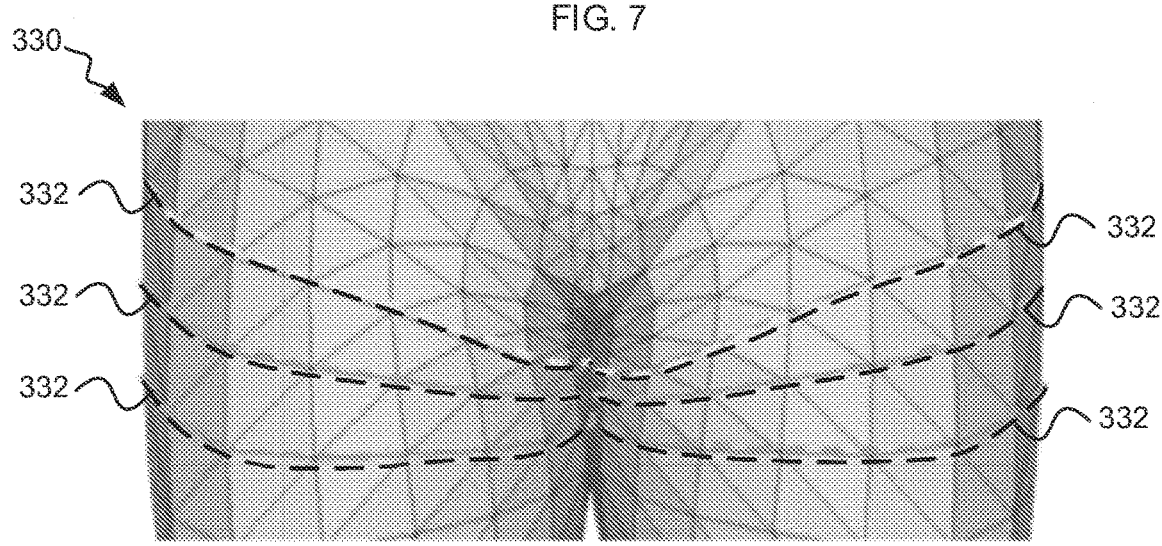
FIG. 8 illustrates a schematic representation of measurement paths around the thighs of a registered mesh according to an embodiment.

FIG. 8 illustrates a schematic representation of measurement paths 332 around the thighs of a registered mesh 330 according to an embodiment. The raw measurement results may be calculated in a similar fashion as in the embodiment of FIG. 7. Since the registered mesh 330 comprises two thighs, the six raw measurement results corresponding to the six measurement paths 332 may be used to calculate a single measurement result in the regression optimisation process. Alternatively, the three raw measurement results of each thigh may be used to calculate a separate measurement result for each thigh.

Figure 9:
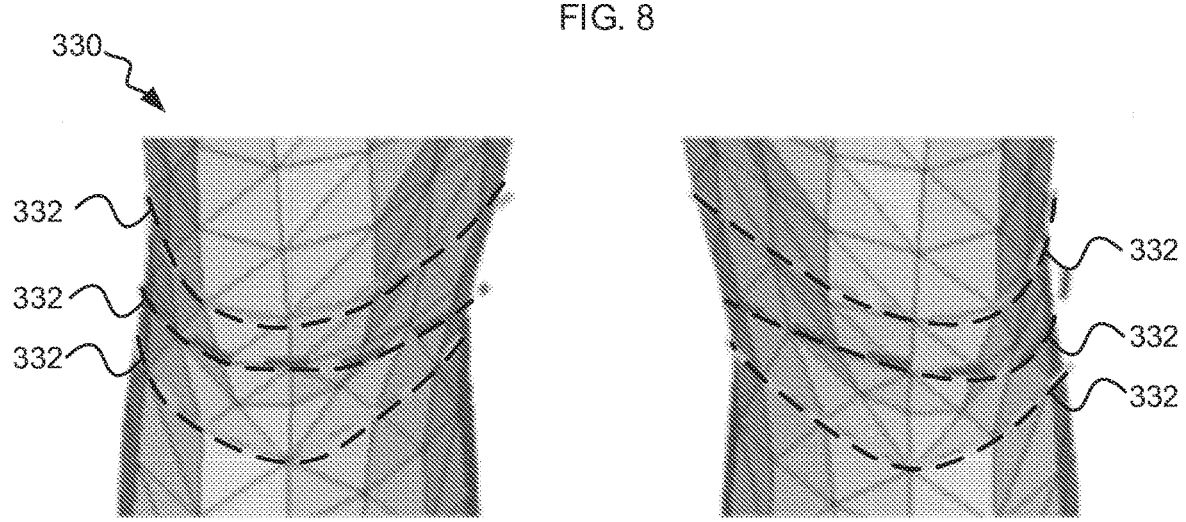
FIG. 9 illustrates a schematic representation of measurement paths around the knees of a registered mesh according to an embodiment.

FIG. 9 illustrates a schematic representation of measurement paths 332 around the knees of a registered mesh 330 according to an embodiment. Similar observations to those presented above with respect to the embodiments of FIG. 7 and FIG. 8 apply also to this embodiment.

Figure 10:
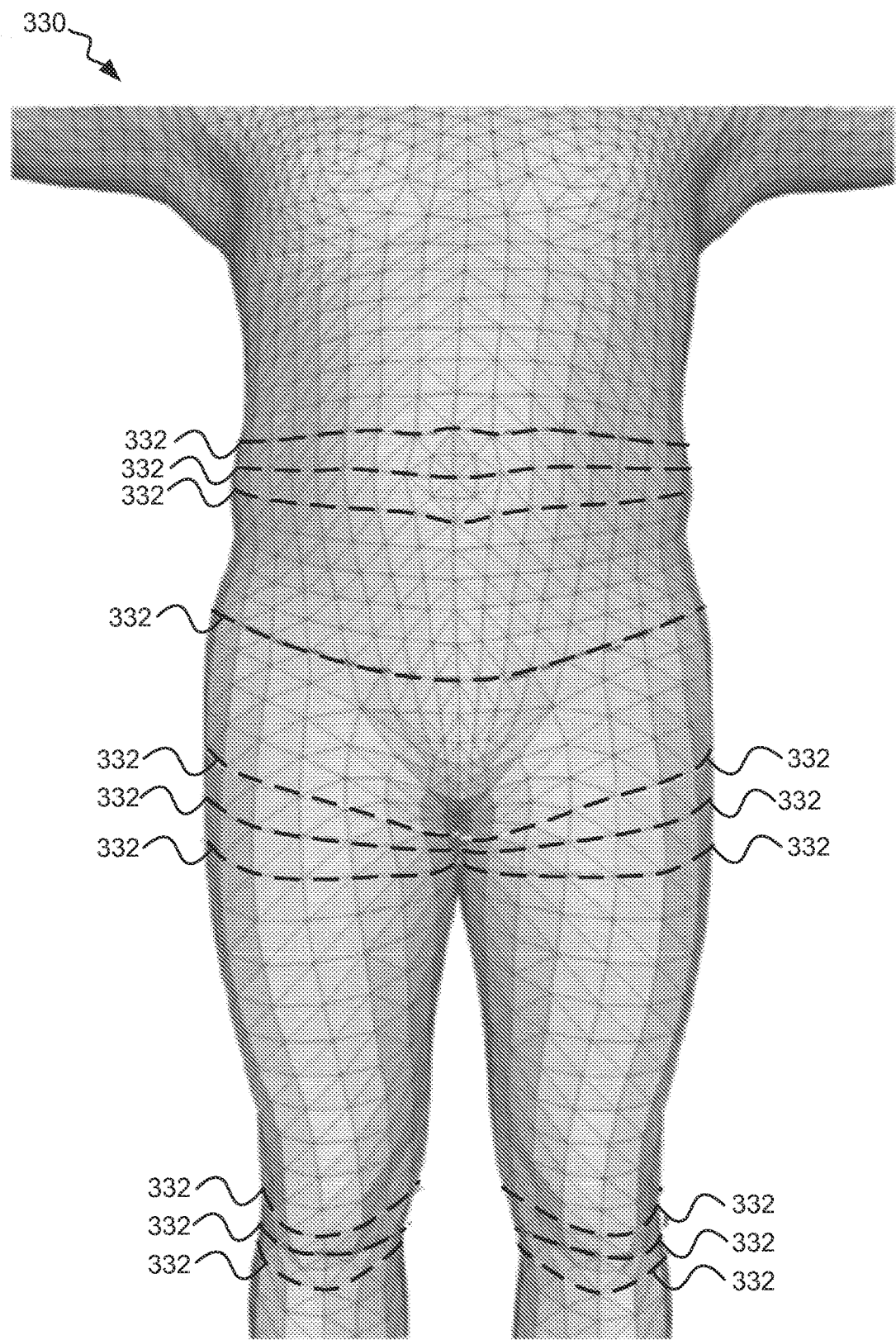
FIG. 10 illustrates a schematic representation of measurement paths around various body parts of a registered mesh according to an embodiment.

FIG. 10 illustrates a schematic representation of measurement paths 332 around various parts of the registered mesh 330. In addition to the measurement paths 332 around the abdomen, the thighs, and the knees of the registered mesh 330, FIG. 10 further illustrates a measurement path 332 around the waist of the registered mesh 330. It should be appreciated that a single point cloud 310 may be used to generate the registered mesh 330, and all of the measurement results presented in FIG. can be obtained from this single registered mesh 330. Furthermore, if the template mesh 320 comprises any number of measurement paths, all of the corresponding raw measurement results may be obtained from a single registered mesh 330. Thus, a single scan of a human body may be used to measure all relevant measurements.

The geodesic distances on 3D triangular structure meshes, such as the registered mesh 330, are similar to many standard physical anthropometric clothing (tailor) measurements. A geodesic distance on the registered mesh 330 may correspond to a predetermined measurement path 332.

For each surface distance measurement $t_i$, also referred to as an anthropometric clothing measurement, a set of raw measurement results $t_i^{(1)}, \ldots, t_i^{(C)}$ can be defined. The raw measurement results may also be referred to as surface circumference path lengths. The raw measurements can be measured in the model space after the registration process. The paths can be defined as sets of vertices 333 in the model $P_i^c = \{v_1^c, v_2^c, \ldots, v_m^c\}$ that define a circular path. Consequently, 3D length and circumference measurements can be extracted from the set of registered 3D meshes as "raw anthropometric clothing measurements". The length of a circumference path can be calculated as the total length of the edges 334 that the measurement path 332 goes through in the registered mesh 330. For each surface distance measurement, few similar measurement paths 332 can be selected in order to extract more local deformation features. The reason why multiple paths could be selected is that it is not certain to find a set of edges 334 or vertices 333 that match exactly to the desired measurements.

According to an embodiment, the regression optimisation comprises one of: linear regression; stepwise linear regression; support vector regression, SVR; non-linear SVR; ridge regression; polynomial regression; stepwise regression; elastic net regression; Gaussian process regression; binary regression decision tree; and multi-regression tree.

The purpose of the regression optimisation stage may be to find a non-linear or linear mapping $f(\bullet)$ such that $$f(P_i):(t_i^{(1)}, \ldots, t_i^{(C)}) \mapsto \hat{t}_i$$

i.e. the function $f$ maps the raw surface measurement results $t_i^{(j)}$ to $\hat{t}_i$ which is an estimate of the true surface distance measurement $t_i$. $\hat{t}_i$ may also be referred to as a measurement result. For this purpose, many existing regression methods can be used: linear regression is an approach for modelling the relationship between multiple explanatory variables denoted X and a scalar dependent variable y which can be represented in the mathematical form as $$\hat{y}_i = \beta_0 \times 1 + \beta_1 \times x_{i,1} + \ldots + \beta_p \times x_{i,p} + \epsilon_i.$$

To find coefficients β, least square estimation can be employed to minimise the sum of squared errors as below:

$$\min \sum_{i=1}^{m} (y_i - \hat{y}_i)^2 = \min \sum_{i=1}^{m} (y_i - (\beta x_i + \epsilon_i))^2$$

Support vector regression, SVR, is another supervised learning model which analyses data used for regression and employs the same principles as the support vector machine, SVM. The non-linear SVR could be represented as:

$$y = \sum_{i=1}^{N} (\alpha_i - \alpha_i^*) K(x_i, x) + b,$$

where K(•) denotes the kernel functions, for example polynomial or Gaussian functions, which transform the data into a higher dimensional feature space to make it possible to perform the linear separation. α is the Lagrange multiplier.

The linear SVR could be written as a convex optimization problem with a weight vector w and a margin of tolerance $\epsilon$:

$$\min \frac{1}{2} \|w\|^2$$
$$\text{s.t.:} \quad y_i - wx_i - b \leq \epsilon$$
$$wx_i + b - y_i \leq \epsilon$$

Ridge regression is also a technique for analysing multiple regression data that suffer from multicollinearity. The regression equation can be written in matrix form as:

$$Y = X\beta + e$$

where β is the regression coefficients to be estimated, and e represents the errors or residuals. The coefficients β can be obtained by:

$$\hat{\beta} = (X^T X + kI)^{-1} X^T Y,$$

where k is the ridge parameter and I is the identity matrix. Small positive values of k, for example less than one, can improve the conditioning of the problem and reduce the variance of the estimates. While biased, the reduced variance of ridge estimates often result in a smaller mean square error when compared to least-squares estimates.

Decision tree learning approach can be also utilized to create a model that predicts the value of a target variable based on several inputs. Similarly polynomial regression, stepwise regression, elastic net regression and other existing methods are all feasible candidates.

Mean absolute error, MAE, can be employed as the error metric between the ground truth and obtained measurement results. The ground truth may be any measurement method that may be considered to give reliable results. For example, in the case of anthropometric clothing measurements, the ground truth may be a measurement done by a tailor. For each measurement of a local part i, Mean Absolute Error $\epsilon_i$, over all subjects j can be obtained as $$\epsilon_i = \frac{1}{|j|} \sum_{j=1}^{|j|} |t_i^{(j)} - \hat{t}_i^{(j)}|.$$

Here, |j| denotes the number of subjects j.

FIG. 11 illustrates a schematic representation of a table of estimation accuracies according to an embodiment. In all cases presented in FIG. 11, the number of surface measurements was optimised for each anthropometric measurement, and a non-linear SVR regressor was used. For both men and women, the best performing measurement was neck circumference with 92% test cases below the threshold (6 mm) for men and 80% for women. The worst performing measure was ankle circumference for which only 29% of male test samples and 27% of female succeeded. It turns out that significant source of large estimation errors can be in the body scanning procedure, where certain body parts are sometimes poorly captured. For example, feet regions often lack point cloud points and this can cause the registration step to provide a wrong solution.

Figure 12:
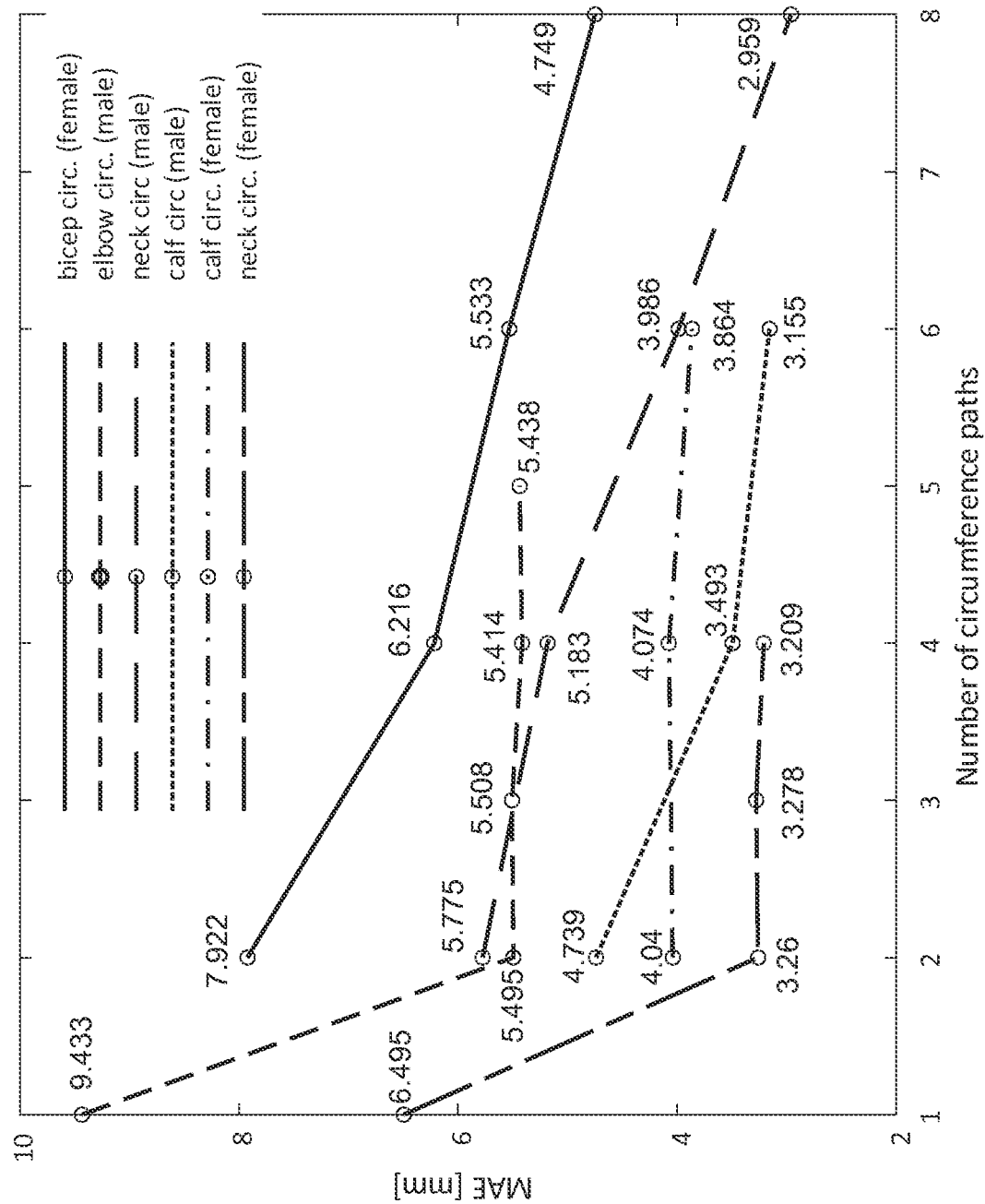
FIG. 12 illustrates a schematic representation of measurement errors according to an embodiment.
Figure 13:
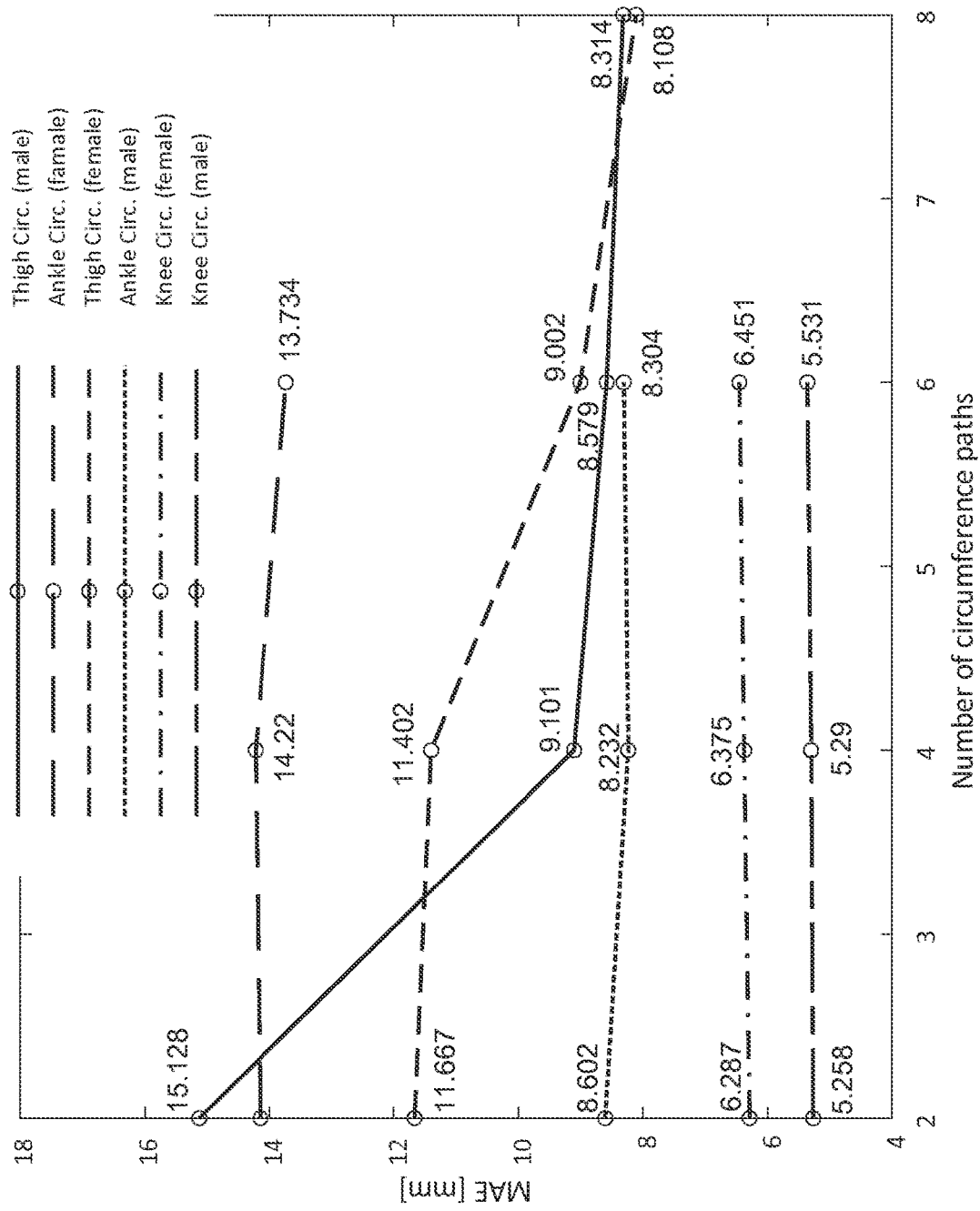
FIG. 13 illustrates a schematic representation of measurement errors according to another embodiment.

FIGS. 12 and 13 illustrate a schematic representation of measurement errors according to an embodiment. FIGS. 12 and 13 show the effect of adding multiple measurement paths (circumference paths) to the regression optimisation. The results for three well and three poorly performing measurements for both males and females are shown in FIGS. 12 and 13. Results are for non-linear SVR regressor with 5-fold cross-validation. The most important findings may be that additional paths generally improve the accuracy and, depending on the measurement, the results can saturate at 3 to 9 measurement paths. In particular, paths close to the true anthropometric measurement strongly contribute to the final accuracy.

FIG. 14 illustrates a schematic representation of mean absolute errors for different regression procedures according to an embodiment. The presented linear regressors are linear regression, stepwise linear regression and ridge regression, and more recent regression methods are elastic net linear Regression, Gaussian process regression, GPR, binary regression decision tree, BRDT, multi-regression tree, multi-tree, linear support vector Regression, SVR, and non-linear SVR. The mean accuracies and success rates for these methods are shown in FIG. 14. Based on these results the linear regressors (linear regression, ridge regression and stepwise linear regression) all perform well and non-linear SVR and Gaussian Process Regression also perform well. They all may be safe choices for regressing measurement results from raw measurement results.

While the procedures presented in this disclosure are particularly applicable for producing measurements related to clothes making, the obtained measurement results may be used also in other ways, for example in body composition analysis.

The apparatus may be implemented in software, hardware, application logic or a combination of software, hardware and application logic. The application logic, software or instruction set may be maintained on any one of various conventional computer-readable media. A "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer. The exemplary embodiments can store information relating to various processes described herein. This information can be stored in one or more memories, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The databases may be located on one or more devices comprising local and/or remote devices such as servers. The processes described with respect to the exemplary embodiments can include appropriate data structures for storing data collected and/or generated by the processes of the devices and subsystems of the exemplary embodiments in one or more databases.

All or a portion of the exemplary embodiments can be implemented using one or more general purpose processors, microprocessors, digital signal processors, micro-controllers, and the like, programmed according to the teachings of the exemplary embodiments, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

The different functions discussed herein may be performed in a different order and/or concurrently with each other.

Any range or device value given herein may be extended or altered without losing the effect sought. Also any embodiment may be combined with another embodiment unless explicitly disallowed.

Although the subject matter has been described in language specific to structural features and/or acts, it is to be understood that the subject matter defined in the appended claims is not necessarily limited to the specific features or acts described above. Rather, the specific features and acts described above are disclosed as embodiments of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The term 'comprising' is used herein to mean including the method, blocks or elements identified, but that such blocks or elements do not comprise an exclusive list and a method or apparatus may contain additional blocks or elements.

It will be understood that the above description is given by way of example only and that various modifications may be made by those skilled in the art. The above specification, embodiments and data provide a complete description of the structure and use of the embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. An apparatus for measuring surface distances on human bodies, the apparatus comprising at least one processor and at least one memory comprising computer program code, wherein the at least one memory and the computer program code being configured to, with the at least one processor, cause the apparatus to at least:

receive a point cloud representing a surface shape of a scanned human body;

generate a registered mesh of the surface shape of the scanned human body by registering a template mesh, representing a reference shape of a human body, onto the point cloud, wherein the template mesh comprises predefined measurement paths, and wherein the registered mesh also comprises the predefined measurement paths;

generate raw measurement results using the predefined measurement paths, wherein each raw measurement result in the raw measurement results corresponds to a measurement path in the predefined measurement paths;

calculate, using non-linear support vector regression, at least one measurement result corresponding to a surface distance on the scanned human body using the raw measurement results; and register the template mesh onto the point cloud by determining a mapping that maps the template mesh onto the point cloud, wherein the mapping minimises a cost function, wherein the cost function comprises a stiffness term, and wherein the stiffness term indicates a similarity of transformations applied to neighbouring vertices of the template mesh in the mapping.

2. The apparatus according to claim 1, further comprising at least one scanning device for scanning shapes of human bodies; wherein the at least one memory and the computer program code is further configured to, with the at least one processor, cause the apparatus to:

use the scanning device for obtaining the point cloud.

3. The apparatus according to claim 2, wherein each measurement path in the predefined measurement paths comprises edges between vertices of the registered mesh.

4. The apparatus according to claim 2, wherein the at least one memory and the computer program code is further configured to, with the at least one processor, cause the apparatus to, before generating the registered mesh:

pre-align the point cloud and the template mesh.

5. The apparatus according to claim 2, wherein the at least one memory and the computer program code is further configured to, with the at least one processor, cause the apparatus to:

pre-align a z-coordinate of a lowest point of the point cloud and a z-coordinate of a lowest point of the template mesh, wherein a z-axis is substantially parallel with a height direction of the scanned human body.

6. The apparatus according to claim 1, wherein each measurement path in the predefined measurement paths comprises edges between vertices of the registered mesh.

7. The apparatus according to claim 6, wherein the at least one memory and the computer program code is further configured to, with the at least one processor, cause the apparatus to, before generating the registered mesh:

pre-align the point cloud and the template mesh.

8. The apparatus according to claim 6, wherein the at least one memory and the computer program code is further configured to, with the at least one processor, cause the apparatus to:

pre-align a z-coordinate of a lowest point of the point cloud and a z-coordinate of a lowest point of the template mesh, wherein a z-axis is substantially parallel with a height direction of the scanned human body.

9. The apparatus according to claim 1, wherein the at least one memory and the computer program code is further configured to, with the at least one processor, cause the apparatus to, before generating the registered mesh:

pre-align the point cloud and the template mesh.

10. The apparatus according to claim 1, wherein the at least one memory and the computer program code is further configured to, with the at least one processor, cause the apparatus to:

pre-align a z-coordinate of a lowest point of the point cloud and a z-coordinate of a lowest point of the template mesh, wherein a z-axis is substantially parallel with a height direction of the scanned human body.

11. The apparatus according to claim 1, wherein each measurement path in the predefined measurement paths is indicated by a vertex identification, ID.

12. The apparatus according to claim 1, wherein the at least one memory and the computer program code is further configured to, with the at least one processor, cause the apparatus to:

register the template mesh onto the point cloud using a non-rigid iterative closest point, ICP, procedure.

13. The apparatus according to claim 1, wherein the cost function comprises a distance term, wherein the distance term comprises distances, and wherein each distance in the distances corresponds to a distance between a point in the point cloud and a corresponding point in the template mesh.

14. The apparatus according to claim 1, further configured to use the at least one measurement result in finding a fitting garment for the scanned human body.

15. The apparatus according to claim 1, further configured to use the at least one measurement result in producing a garment for the scanned human body.

16. A method comprising:

receiving a point cloud representing a surface shape of a scanned human body;

generating a registered mesh of the surface shape of the scanned human body by registering a template mesh, representing a reference shape of a human body, onto the point cloud, wherein the template mesh comprises predefined measurement paths, and wherein the registered mesh also comprises the predefined measurement paths;

generating raw measurement results using the predefined measurement paths, wherein each raw measurement result in the raw measurement results corresponds to a measurement path in the predefined measurement paths;

calculating, using non-linear support vector regression, at least one measurement result corresponding to a surface distance on the scanned human body using the raw measurement results; and registering the template mesh onto the point cloud by determining a mapping that maps the template mesh onto the point cloud, wherein the mapping minimises a cost function, wherein the cost function comprises a stiffness term, and wherein the stiffness term indicates a similarity of transformations applied to neighbouring vertices of the template mesh in the mapping.

17. A computer program product comprising at least one computer-readable medium bearing computer program code which, when executed by a computer, executes the method according to claim 16.

* * * * *